(12) United States Patent
Florio et al.

(10) Patent No.: US 6,618,619 B1
(45) Date of Patent: Sep. 9, 2003

(54) METHOD AND APPARATUS FOR REDUCING THE EFFECT OF EVOKED RESPONSES ON POLARIZATION MEASUREMENTS IN AN AUTOMATIC CAPTURE PACING SYSTEM

(75) Inventors: Joseph J. Florio, La Canada, CA (US); Gene A. Bornzin, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 09/670,243

(22) Filed: Sep. 26, 2000

Related U.S. Application Data

(60) Provisional application No. 60/203,987, filed on May 12, 2000.

(51) Int. Cl.$^7$ ................................................ A61N 1/365
(52) U.S. Cl. ........................................... 607/27; 607/28
(58) Field of Search ........................ 607/27, 28, 11, 607/7, 8, 9

(56) References Cited

U.S. PATENT DOCUMENTS

| | | | |
|---|---|---|---|
| 4,537,201 A | 8/1985 | Delle-Vedove et al. | ...... 128/697 |
| 5,330,512 A | 7/1994 | Hauck et al. | |
| 5,417,718 A | 5/1995 | Kleks et al. | |
| 5,466,254 A | 11/1995 | Helland | |
| 5,476,487 A * | 12/1995 | Sholder | ............ 607/28 |
| 5,741,312 A | 4/1998 | Vonk et al. | ............ 607/28 |
| 5,843,136 A | 12/1998 | Zhu et al. | |
| 5,861,012 A | 1/1999 | Stroebel | |
| 6,175,766 B1 * | 1/2001 | Bornzin | ............ 607/28 |

* cited by examiner

Primary Examiner—George R. Evanisko
Assistant Examiner—Roderick Bradford

(57) ABSTRACT

An initial polarization measurement is made by applying two electrical calibration pulses to the heart separated by a first time period. The first pulse is sufficient to generate an evoked response. The second pulse is applied during a refractory period associated with the first pulse. A polarization measurement is made following the second pulse and compared against a predetermined threshold. If the polarization does not exceed the threshold, the evoked response is adjusted using the measured polarization and an automatic capture function of the pacing system is programmed using the adjusted evoked response. However, if the polarization exceeds the threshold, a second pair of pulses are applied to the heart separated by a second time period, different from the first time period. A second polarization measurement is made after the second pulse and, if the second measured polarization does not exceed the predetermined threshold, the evoked response is adjusted using the newly measured polarization and the automatic capture function is programmed using the adjusted evoked response. If the polarization measurement again exceeds the predetermined threshold, the automatic capture function is disabled. Alternatively, a sequence of three pulses are applied to the heart and polarization is measured after the second and third pulses or calibration pulses may be applied after intrinsic depolarization events such as QRS complexes.

26 Claims, 10 Drawing Sheets

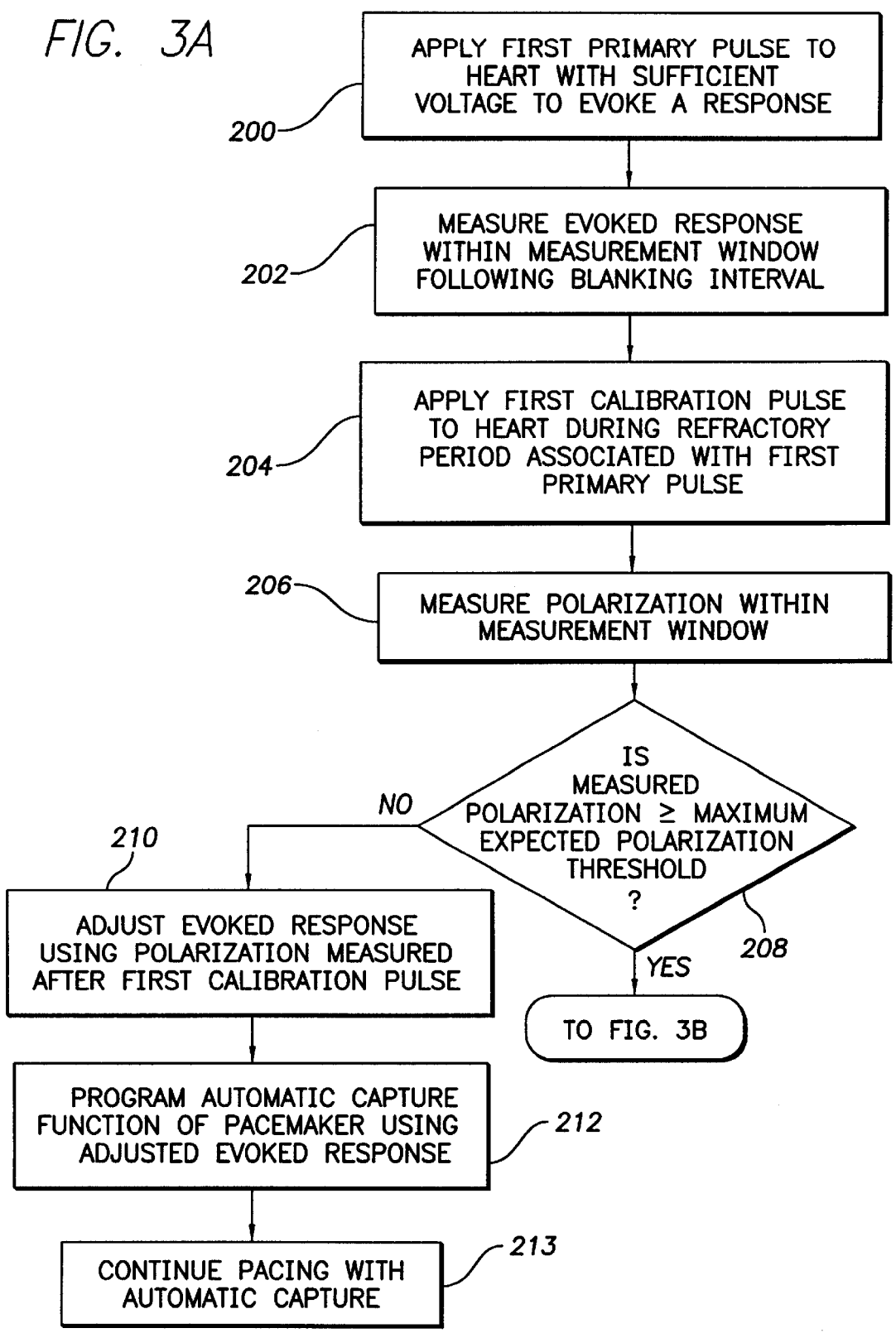

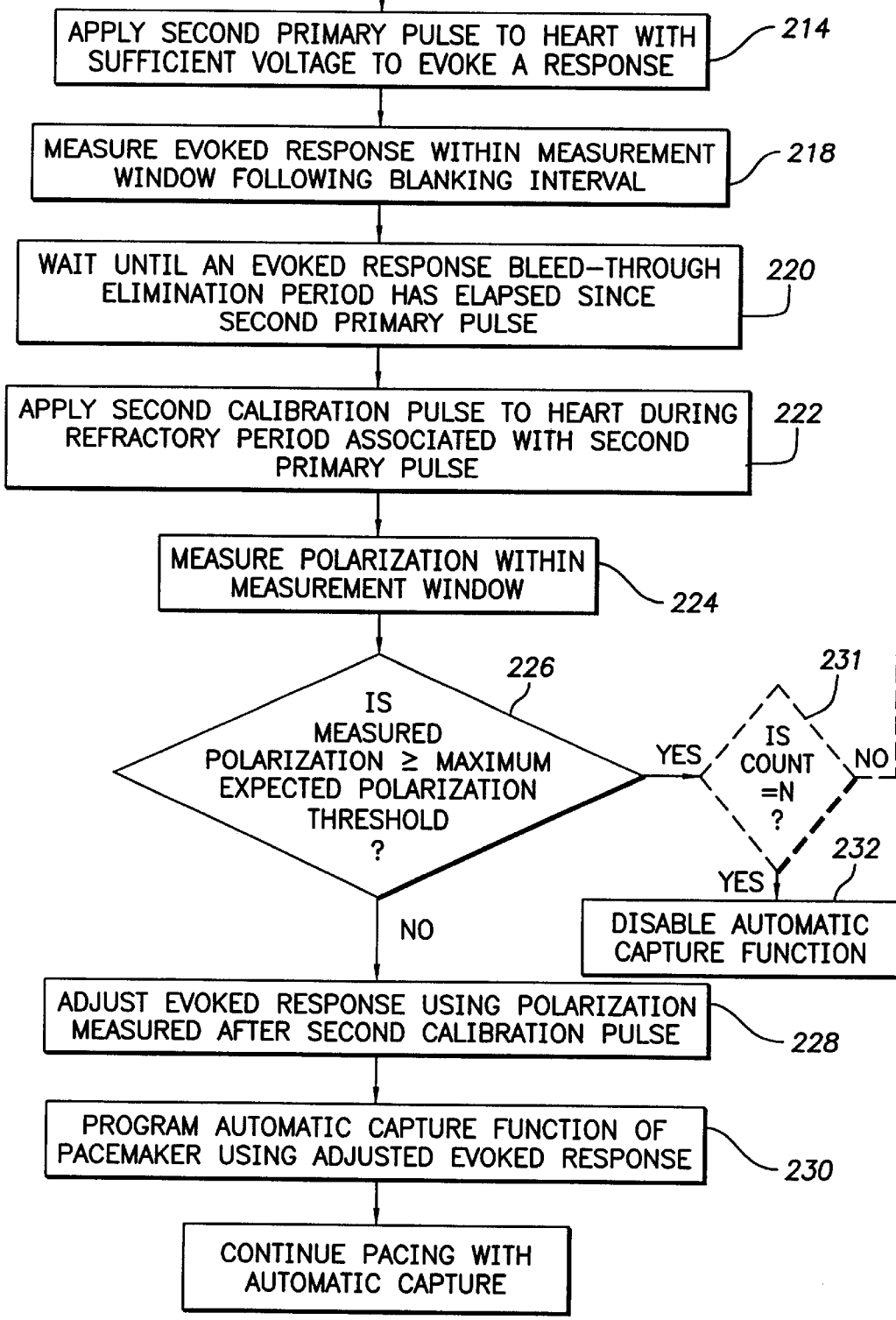

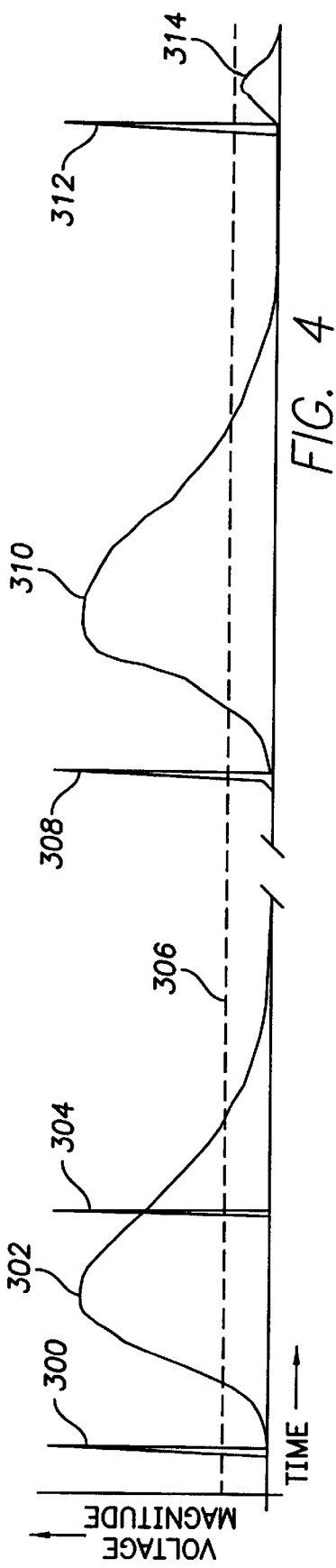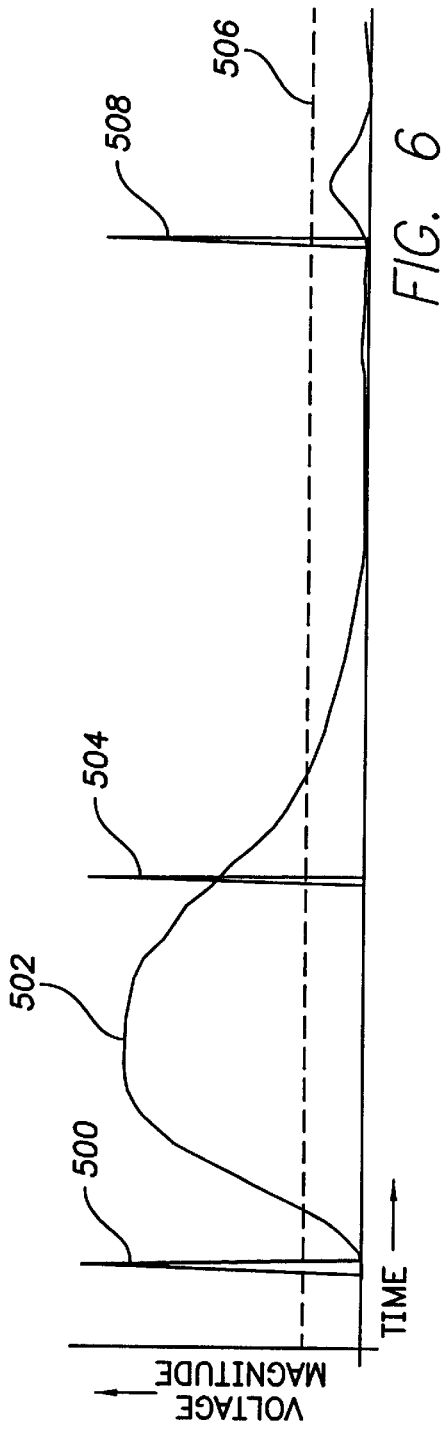

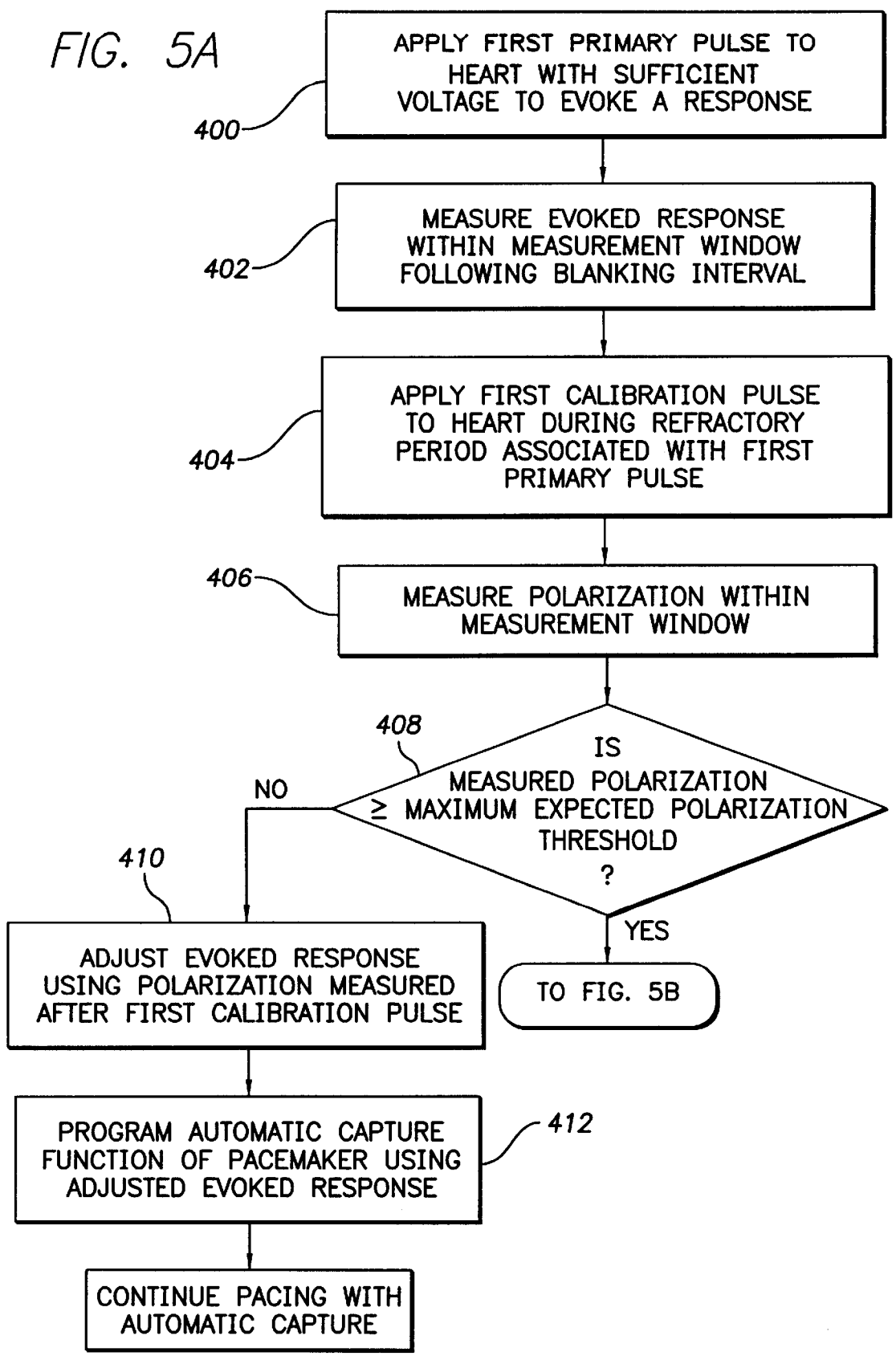

METHOD AND APPARATUS FOR REDUCING THE EFFECT OF EVOKED RESPONSES ON POLARIZATION MEASUREMENTS IN AN AUTOMATIC CAPTURE PACING SYSTEM

This application claims the benefit of U.S. Provisional Application 60/203,987, filed May 12, 2000.

BACKGROUND OF THE INVENTION

The invention generally relates to pacemakers or other implantable cardiac stimulation devices and in particular to techniques for reducing the effects of evoked response bleed-through on electrical polarization measurements performed in connection with calibrating an automatic capture system of an implantable cardiac stimulation device, e.g., a pacemaker, an implantable cardioverter/defibrillator (ICD), or the like.

DESCRIPTION OF RELATED ART

A pacemaker is a medical device, typically implanted within a patient, that provides electrical stimulation pulses to selected chambers of the heart, i.e., the atria and/or the ventricles. Such stimulation pulses cause the muscle tissue of the heart (myocardial tissue) to depolarize and contract, thereby causing the heart to beat at a controlled rate.

Most pacemakers can be programmed to operate in a demand mode of operation, i.e., to generate and deliver stimulation pulses to the heart only when the heart fails to beat on its own. To this end, the pacemaker senses cardiac activity, i.e., heart beats, and if the heart beats do not occur at a prescribed rate, then stimulation pulses are generated and delivered to an appropriate heart chamber, either an atrium or a ventricle, in order to force the heart to beat.

When operating in a demand mode of operation, the pacemaker defines a period of time, referred to generally as the "escape interval" (which may further be referred to as either an "atrial escape interval" or a "ventricular escape interval," depending upon the mode of operation of the pacemaker) that is slightly longer than the period of time between normal heart beats. Upon sensing such a "natural" (non-stimulated or non-paced) heart beat within the allotted time period, the escape interval is reset, and a new escape interval is started. A stimulation (or pacing) pulse is generated at the conclusion of this new escape interval unless a natural heart beat is again sensed during the escape interval. In this way, stimulation pulses are generated "on demand," i.e., only when needed to maintain the heart rate at a rate that never drops below the rate set by the escape interval.

The heart rate is monitored by examining the electrical signals that are manifest concurrent with the depolarization or contraction of the myocardial tissue. The contraction of atrial muscle tissue is manifest by the generation of a P-wave. The contraction of ventricular muscle tissue is manifest by the generation of an R-wave (sometimes referred to as the "QRS complex"). The sequence of electrical signals that represent P-waves followed by R-waves (or QRS complexes) can be sensed from inside of or proximate to the heart by using sensing leads implanted inside or on the heart, e.g., pacemaker leads, or by using external electrodes attached to the skin of the patient.

Most modern implantable pacemakers are programmable. That is, the basic escape interval (atrial and/or ventricular) of the pacemaker, as well as the sensitivity (threshold level) of the sensing circuits used in the pacemaker to sense P-waves and/or R-waves, and numerous other operating parameters of the pacemaker, may be programmably set at the time of implantation or thereafter to best suit the needs of a particular patient. Hence, the pacemaker can be programmed so as to yield a desired performance.

The operation of a pacemaker as described above presupposes that a stimulation pulse generated by the pacemaker effectuates capture. As used herein, the term "capture" refers to the ability of a given stimulation pulse generated by a pacemaker to cause depolarization of the myocardium, i.e., to cause the heart muscle to contract, or to cause the heart to "beat." A stimulation pulse that does not capture the heart is thus a stimulation pulse that may just as well have not been generated, since it has not caused the heart to beat. Such a non-captured stimulation pulse not only represents wasted energy—energy drawn from a limited energy resource (e.g., a battery) of the pacemaker—but worse still may provide the pacemaker logic circuits with false information. That is, the logic circuits of the pacemaker may presuppose that each stimulation pulse generated by the pacemaker captured the heart. If the stimulation pulse does not capture the heart, then the pacemaker logic circuits control the operation of the pacemaker may be based on false information, and may thus control the pacemaker in an inappropriate manner. Thus, there is a critical need for a pacemaker to properly determine whether a given stimulation pulse has effectuated capture.

While there are many factors that influence whether a given stimulation pulse effectuates capture, a principal factor is the energy of the stimulation pulse. The energy of the stimulation pulse, in turn, is determined by the amplitude and width of the stimulation pulse generated by the pacemaker. Advantageously, in a programmable pacemaker, both the amplitude and pulse width of the stimulation pulse are parameters that may be programmably controlled or set to a desired value.

An implantable pacemaker derives its operating power, including the power to generate a stimulation pulse, from a battery. The power required to repeatedly generate a stimulation pulse dominates the total power consumed by a pacemaker. Hence, to the degree that the power associated with the stimulation pulse can be minimized, the life of the battery can be extended and/or the size and weight of the battery can be reduced. Unfortunately, however, if the power associated with a stimulation pulse is reduced too far, the stimulation pulse is not able to consistently effectuate capture, and the pacemaker is thus rendered ineffective at performing its intended function. Thus, it is desirable for a pacemaker to adjust the energy of a stimulation pulse to an appropriate level that provides sufficient energy to effectuate capture, i.e., generate an evoked response, but does not expend any significant energy beyond that required to effectuate capture.

Initially, the most common technique used to adjust the stimulation energy to an appropriate level was manual, using the programmable features of the pacemaker. That is, at the time of implant, a cardiologist or other physician conducts some preliminary stimulation tests to determine how much energy a given stimulation pulse must have to effectuate capture at a given tissue location. If the preliminary tests indicate that the capture threshold is high (compared to the average patient) then the lead will be repositioned until a "good" threshold is found. Once it has been determined that the thresholds are acceptable, the stimulation electrode is then left in place and the amplitude and/or width of the stimulation pulse is set to a level that is typically 2 to 3 times greater than the amplitude and/or width determined in the preliminary tests. The increase in energy above and beyond the energy needed to effectuate capture is considered as a "safety margin."

During the acute phase, e.g., over a period of days or weeks after implant, the stimulation pulse energy needed to effectuate capture usually changes. This stimulation pulse energy is hereafter referred to as the "capture-determining threshold." Hence, having a safety margin factored into the stimulation pulse energy allows the stimulation pulses generated by the pacemaker to continue to effectuate capture despite changes in the capture-determining threshold. Unfortunately, however, much of the energy associated with the safety margin represents wasted energy, and shortens the life of the battery. Furthermore, after the acute phase (when the lead is considered in the chronic phase), the capture-determining threshold is typically much lower than that determined at implant. Thus, if left unchecked, the safety margin determined necessary at implant is extremely wasteful during the chronic phase.

State of the art pacemakers now include an automatic capture system (see, for example the AUTOCAPTURE™ pacing system used by Pacesetter, Inc., which, after implant of the pacemaker, automatically determines the capture-determining threshold and sets the stimulation pulse energy accordingly. The automatic capture system also periodically redetermines the capture-determining threshold and re-sets the stimulation pulse energy. Hence, if the threshold increases with time, the stimulation pulse energy is increased as needed to maintain capture. Alternatively, if the threshold decreases with time, the stimulation pulse energy is decreased as needed so that energy is not needlessly wasted.

A typical automatic capture system operates by applying a sequence of stimulation pulses to the heart tissue with differing pulse energy amounts and determines the lowest stimulation pulse energy sufficient to effectuate capture. To determine if capture has been effectuated by a stimulation pulse, the automatic capture system looks for an evoked response (ER) following the pulse. If no evoked response is detected, the pacemaker thereby concludes that the stimulation pulse did not have sufficient energy to effectuate capture. If an evoked response is detected, however, the pacemaker thereby concludes that the stimulation pulse had sufficient energy to effectuate capture.

More specifically, when capture occurs, the evoked response is represented by an intra-cardiac P-wave or R-wave (which typically has a different morphology, or wave shape, than does an intrinsic P-wave or R-wave which results from natural cardiac contractions) that indicates contraction of the respective cardiac tissue in response to the applied stimulation pulse. For example, using such an evoked response technique, if a stimulation pulse (hereafter referred to as a V-Pulse) is applied to the ventricle, any response sensed by the ventricular sensing circuits of the pacemaker immediately following the application of the V-Pulse is assumed to be an evoked response that evidences ventricular capture. Similarly, if a stimulation pulse (hereinafter referred to as an A-Pulse) is applied to the atrium, any response sensed by the atrial sensing circuits of the pacemaker immediately following the application of the A-Pulse is assumed to be an evoked response that evidences atrial capture. A specific automatic capture system is described in detail within U.S. Pat. No. 5,417,718 (Kleks et al.) which is incorporated by reference herein.

One problem with evoked response detection is that the signal sensed by the ventricular and/or atrial sensing circuits immediately following the application of a V-Pulse and/or A-Pulse may not be an evoked response. Rather, it may be noise, either electrical noise caused, for example, by electromagnetic interference (EMI), or myocardial noise caused by random myocardial or other muscle contractions (muscle "twitching"). Alternatively, that which is sensed by the ventricular and/or atrial sensing circuits may be a natural intrinsic R-wave or P-wave that just happens to occur immediately following the application of the non-capturing V-Pulse or A-Pulse.

Another signal that interferes with the detection of an evoked response, and potentially the most difficult to deal with because it is usually present in varying degrees, is lead polarization. Lead polarization is caused by electrochemical reactions that occur at the lead/tissue interface due to the application of the electrical stimulation pulse, A-Pulse or V-Pulse, across such interface. (The lead/tissue interface is that point where the electrode of the pacemaker lead contacts the cardiac tissue. Such a point is normally inside the atrium or the ventricle, assuming endocardial stimulation leads are employed.) Unfortunately, because the evoked response is sensed through the same electrode through which the A-Pulse or V-Pulse is delivered, the resulting polarization signal present at such electrode can corrupt the evoked response sensed by the sensing circuits of the pacemaker. To make matters worse, the lead polarization signal is not easily characterized. It is a complex function of the lead materials, lead geometry, tissue impedance, stimulation energy, and many other variables, most of which are continually changing over time.

In each case, the result is the same—a potentially false positive detection of the evoked response. Such a false positive detection leads to a false capture indication, which in turn can lead to missed heartbeats, a highly undesirable situation. Accordingly, techniques have been developed for measuring the amount of polarization and then adjusting the detected evoked response using the measured polarization to thereby reduce, or eliminate, the adverse effect of lead polarization on the evoked response.

Insofar as polarization measurements are concerned, state-of-the-art pacemakers typically measure the polarization in vivo by applying two pacemaker pulses to the heart separated by a time less than the natural refractory period of the heart. (The natural refractory period of the heart is that time period following depolarization or contraction of the cardiac tissue during which the cardiac tissue is not capable of depolarizing again. The natural refractory period, which may be thought of as a repolarization period, may vary from 100–200 milliseconds or more.) Typically, the two pulses are applied with a separation of about 60–90 milliseconds. The evoked response is measured after the first pulse in a window of approximately 50 milliseconds that occurs following a blanking window of 6–15 milliseconds. The second pulse occurs while the heart tissue is refractory. Polarization is also measured during the measurement window of about 50 milliseconds following the second pulse but still within the refractory period of the first pulse.

FIG. 1 illustrates a prior art method for measuring polarization based upon two pulses. The first pulse 100 triggers an evoked response 102. The evoked response is measured during a measurement window of 50 milliseconds following a blanking period of 10 milliseconds. Note that the measured evoked response 102 is actually a combination of the actual evoked response and some amount of polarization. To determine the true amount of evoked response by eliminating the polarization component, a second pulse 104 is applied following the evoked response measurement window. Any electrical response occurring following the second pulse is measured during a polarization measurement window of 50 milliseconds immediately following the second pulse. In the example of FIG. 1, a small amount of polarization 106 occurs. The amount of polarization measured is then used to adjust the evoked response amount detected during the evoked response measurement window. The final resulting evoked response amount is employed in programming the automatic capture system of the pacemaker.

It has been found that excessively high polarization readings may occasionally occur, even with leads that typically generate relatively little polarization. It is believed that the high readings are not representative of the true polarization but may be the result of evoked response bleed-through which occurs if the evoked response from the first pulse has not decayed sufficiently prior to measurement of polarization. Other factors that may affect polarization measurements performed following the second pulse include the amplitude of the evoked response, morphology, T-wave amplitude and sense amplifier characteristics.

FIG. 2 illustrates a situation, observed in the prior art, where evoked response bleed-through occurs. Within FIG. 2, a first pulse 110 is applied triggering an evoked response 112. The evoked response is measured during a measurement window of 50 milliseconds in length following a blanking period of 10 milliseconds. A calibration pulse 114 is applied at the end of the measurement window. However, the evoked response has not completely decayed prior to application of calibration pulse 114. Accordingly, any measurements made during a polarization measurement window immediately following the calibration pulse will detect both the polarization and the residual evoked response. As a result, the polarization amount is over-estimated and, when employed to adjust evoked response, the resulting value for the evoked response is incorrect. Hence, the automatic capture mechanism of the pacemaker could be set to an incorrect value.

Accordingly, within typical state-of-the-art pacemakers, the amount of polarization is compared against a maximum expected polarization threshold and, if it exceeds that threshold, the polarization is assumed to be inaccurate and the automatic capture function is disabled, thereby requiring manual threshold setting by a physician.

Another problem that may arise with some conventional polarization measurement techniques is that evoked response bleed-through may also arise based upon responses from intrinsic events. In this regard, it is possible that the second polarization measurement pulse may be delivered following an intrinsic event such as a P-wave or R-wave. If so, some portion of the response from the intrinsic event may affect the polarization measurement. Indeed, as a result of the additional response bleed-through from the intrinsic event, the measured polarization may exceed the cutoff threshold causing the automatic capture function to be disabled.

Hence, in at least some circumstances, the many advantages of the automatic capture system cannot be realized as a result of potentially inaccurate polarization measurements. Accordingly, it would be highly desirable to provide an improved technique for measuring polarization which permits a more accurate and reliable polarization measurement to be made, particularly in circumstances where an initial polarization measurement appears to be inaccurate, and it is to this end that aspects of the invention are primarily directed.

SUMMARY OF THE INVENTION

The invention provides a method and apparatus for determining the amount of polarization occurring following generation of electrical pulses in heart tissue connected to an implantable cardiac stimulation device. In accordance with a first aspect of the invention, a magnitude of electrical polarization is measured within the heart tissue using a first pair of electrical pulses separated by a first amount of time. Then, if the magnitude of electrical polarization exceeds a predetermined threshold, the magnitude is re-measured using a second pair of electrical pulses separated by a second amount of time, different from the first.

In this manner, if a first polarization measurement is high and may be erroneous, a second polarization measurement is automatically made with a greater amount of delay between the primary pulse and the subsequent calibration pulse. If the high initial polarization measurement was the result of evoked response bleed-through, the second measurement should be considerably lower and provide a better estimate of the true polarization. If the second polarization measurement is also high, then the automatic capture system or other features of the pacing device which rely on accurate polarization measurements are disabled. In an exemplary embodiment, the amount of time separating the first pair of pulses is between 60 and 90 milliseconds. The amount of time separating the second pair of pulses is between 40 and 200 milliseconds.

In accordance with a second aspect of the invention, rather than employing two pairs of electrical pulses, a sequence of three consecutive pulses are applied: a primary pulse, a first calibration pulse, and a second calibration pulse. The second calibration pulse is only administered if a polarization measurement made following the first calibration pulse exceeds the predetermined threshold. If so, the second calibration pulse is administered within the refractory period of the primary pulse and a second polarization measurement is made following the second calibration pulse. The second polarization measurement is employed in connection with setting the automatic capture system or other pacing functions requiring an accurate polarization measurement.

In accordance with a third aspect of the invention, the magnitude of electrical polarization is measured within the heart tissue using a polarization calibration pulse administered during a refractory period between an intrinsic depolarization event and a subsequent repolarization event. In one example of the method, an intrinsic QRS complex is detected and then a polarization calibration pulse is administered following a delay period to place the calibration pulse within the refractory period between the QRS complex and the subsequent T-wave. The magnitude of electrical polarization is then measured following the polarization calibration pulse.

Hence, rather than providing a pair of pulses with the first pulse triggering an evoked response and the second pulse triggering a polarization response, the evoked response is generated naturally within the heart. Thus, any possible adverse biological effects that might result from artificial stimulation of an evoked response are avoided.

In a further aspect of the present invention, the delays associated with the delivery of the calibration pulses may be automatically varied, e.g., increased, in order to search for the lowest polarization reading.

Other embodiments may be provided consistent with general principles of the invention. Apparatus embodiments are also provided.

BRIEF DESCRIPTION OF THE DRAWINGS

FIGS. 3A and 3B are flow charts illustrating a method for measuring electrical polarization where two pairs of electrical pulses are employed in accordance with the invention.

FIG. 4 is a timing diagram illustrating the use of the two pairs of electrical pulses of the method of FIGS. 3A and 3B.

FIGS. 5A and 5B are flow charts illustrating an alternative method for measuring electrical polarization where three consecutive electrical pulses are employed.

FIG. 6 is a timing diagram illustrating the use of three consecutive electrical pulses of the method of FIGS. 5A and 5B.

DETAILED DESCRIPTION OF THE INVENTION

Figure 1:
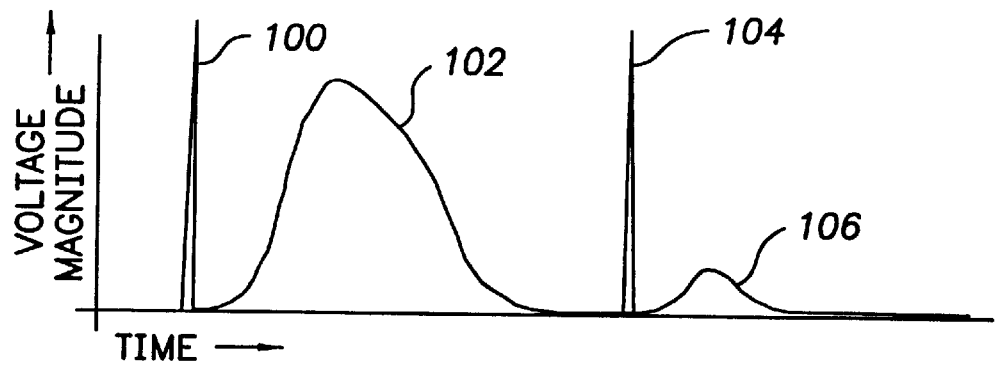
FIG. 1 is a timing diagram or a prior art technique which uses a pair of electrical pulses for measuring evoked response and polarization where the evoked response has decayed to a negligible amount prior to measurement of polarization.
Figure 2:
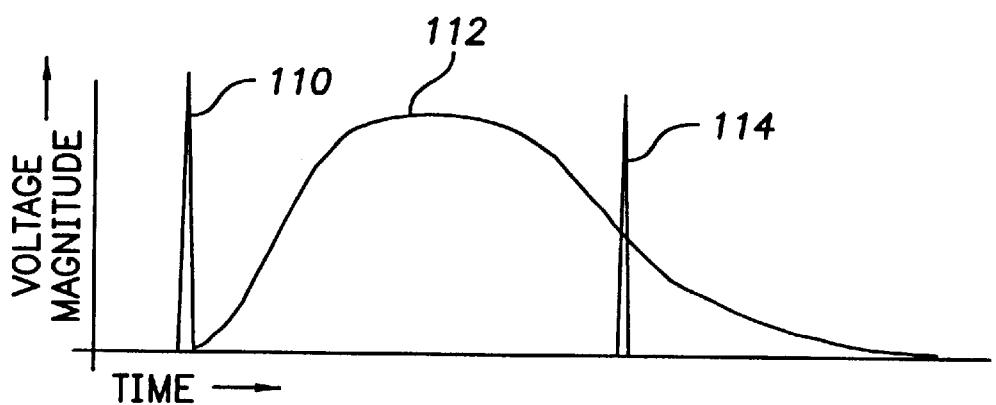
FIG. 2 is a timing diagram a situation, which may be observed in the prior art, where the evoked response has not decayed sufficiently prior to the polarization measurement such that the resulting polarization measurement is erroneous.

With reference to the remaining figures, preferred and exemplary embodiments of the invention will now be described. The embodiments primarily relate to the determination of an amount of polarization for use in adjusting a measured amount of evoked response prior to setting an automatic capture function within an implantable medical device such as a pacemaker. However, principles of invention may be applied in other embodiments as well.

FIGS. 3A and 3B illustrate a method for measuring electrical polarization using two pairs of electrical pulses. Initially, at step 200, a first primary electrical pulse is applied to the heart with a voltage sufficient to generate an evoked response within the heart. To ensure that a response is evoked, the pulse is preferably administered outside of a refractory period occurring following any intrinsic electrical activity within the heart. To this end, although not shown in FIGS. 3A–3B, the system preferably detects intrinsic activity and times the application of the first primary pulse to the heart at the time immediately following completion of a refractory period. The duration of a refractory period is stored within the system. Typically, the refractory period is on the order of about 300 milliseconds.

At step 202, the system then measures the magnitude of the response evoked by the first primary pulse. The evoked response is measured during an evoked response measurement window, e.g., 50 milliseconds, following a blanking window, e.g., 6–15 milliseconds. Preferably, the evoked response is measured and quantified by sampling the voltage within the heart numerous times within the measurement window. Then, an average voltage is calculated from the measured set of individual voltages. Alternatively, other measurements and quantifying techniques may be employed for determining a value representative of the evoked response. Although not shown, the magnitude of the evoked response is compared against a minimum evoked response threshold which is representative of a minimum voltage amount associated with a normal evoked response. If the detected evoked response falls below the minimum threshold, it is assumed that the first, primary pulse did not generate an evoked response, perhaps because the pulse was asserted during a refractory period, and processing returns to step 200 for applying another primary pulse.

If the evoked response achieves the threshold, thereby indicating that the primary pulse succeeded in evoking a response within the heart tissue, step 204 is performed where the pacemaker asserts a first calibration pulse, preferably having a voltage equal to that of the primary pulse. The calibration pulse is asserted following completion of the measurement window associated with the primary pulse so as to occur within the refractory period associated with the evoked response. At step 206, the electrical voltage sensed by the electrodes is measured during a measurement window, e.g., about 50 milliseconds, beginning immediately following the calibration pulse. As with the evoked response, polarization is preferably measured by periodically sampling the voltage detected by the electrodes of the pacemaker during the measurement window and then calculating an average.

At step 208, the measured polarization is compared again to a predetermined maximum expected polarization threshold. If the measured polarization does not exceed the threshold, then processing proceeds to step 210 where the evoked response measured at step 202 is adjusted by the measured amount of polarization to yield an adjusted evoked response. Preferably, the adjusted evoked response is calculated by dividing the measured evoked response by the measured polarization. In other implementations, the polarization amount may instead be subtracted from the measured evoked response. At step 212, the automatic capture mechanism of the pacemaker is then programmed using the adjusted evoked response.

If, however, at step 208 the measured polarization is found to exceed the maximum expected polarization threshold, then execution proceeds to step 214 (see FIG. 3B) where a second primary pulse is applied to the heart. The second primary pulse preferably has the same magnitude and shape as the initial primary pulse applied at step 200. Thereafter, at step 218, the evoked response generated by the second primary pulse is measured within the measurement window, e.g., 50 milliseconds, following a blanking window, e.g., 6–15 milliseconds. Then, at step 220, the pacemaker waits for an evoked response bleed-through elimination period, e.g., about 140 milliseconds, to permit the evoked response to fully decay.

At step 222, a second calibration pulse is applied preferably having the same shape and voltage as the first calibration pulse. At step 224, the polarization associated with the second calibration pulse is measured during a polarization measurement window, e.g., about 50 milliseconds, beginning immediately following the second calibration pulse.

At step 226, the polarization measured following the second calibration pulse is compared with the maximum expected polarization threshold and, if it is below the threshold, execution proceeds to steps 228 and 230 where the evoked response measured. The second primary pulse is adjusted by the polarization measured after the second calibration pulse and where the automatic capture function of the pacemaker is programmed using the adjusted evoked response. Otherwise, processing may proceed to step 232 where the automatic capture function is disabled. Hence, if both polarization measurements exceed the threshold, automatic capture is turned off. This prevents the automatic capture mechanism from being programmed using a high, erroneous polarization measurement that is the result of some other factor besides evoked response bleed-through.

Alternatively, additional "second" primary pulses may be delivered to search for a polarization measurement that is less than the expected polarization threshold. In such an implementation, processing proceeds from step 226 to step 231 where it is determined if the specified number of additional, e.g., N, second primary pulses had been delivered. If not, the process repeats at step 214. When the maximum number of attempts have been met, the automatic capture function is disabled in step 232. In a further alternative, the delay in delivering the second primary pulse in step 214 may be extended in order to search for an acceptably low polarization response.

FIG. 4 illustrates exemplary electrical signals applied to, and detected within, the heart as a result of the steps of FIG. 3. Initially, a first primary pulse 300 evokes a response 302. A first calibration pulse 304 is applied after a first delay period, e.g., 60–90 milliseconds, following the primary pulse 300. However, as can be seen in FIG. 4, the evoked response 302 has not fully decayed prior to the calibration pulse 304. Accordingly, the amount of polarization measured following the calibration pulse 304 includes both polarization and evoked response portions and, hence, exceeds a predetermined polarization threshold 306. Thereby, generation of a second primary pulse 308 is triggered which, in turn, evokes a response 310. A second calibration pulse 312 is asserted after a second delay period, e.g., between 40–200 milliseconds, following the second primary pulse and evokes a polarization response 314. The second delay period is preferably selected to be greater than the first delay period and thus further avoid potential bleed-through. Polarization response 314 is below the polarization threshold 306 and, hence, is used in adjusting evoked response 310 for use in programming the automatic capture system. As can be seen in FIG. 4, by making a second measurement of polarization with a greater spacing between primary pulse 308 and calibration pulse 312, the evoked response 314 associated with the primary pulse fully decays and the evoked response bleed-through does not affect the polarization measurement. As described above, this process may be repeated multiple (N) times to search for an acceptably small polarization response.

Figure 5B:
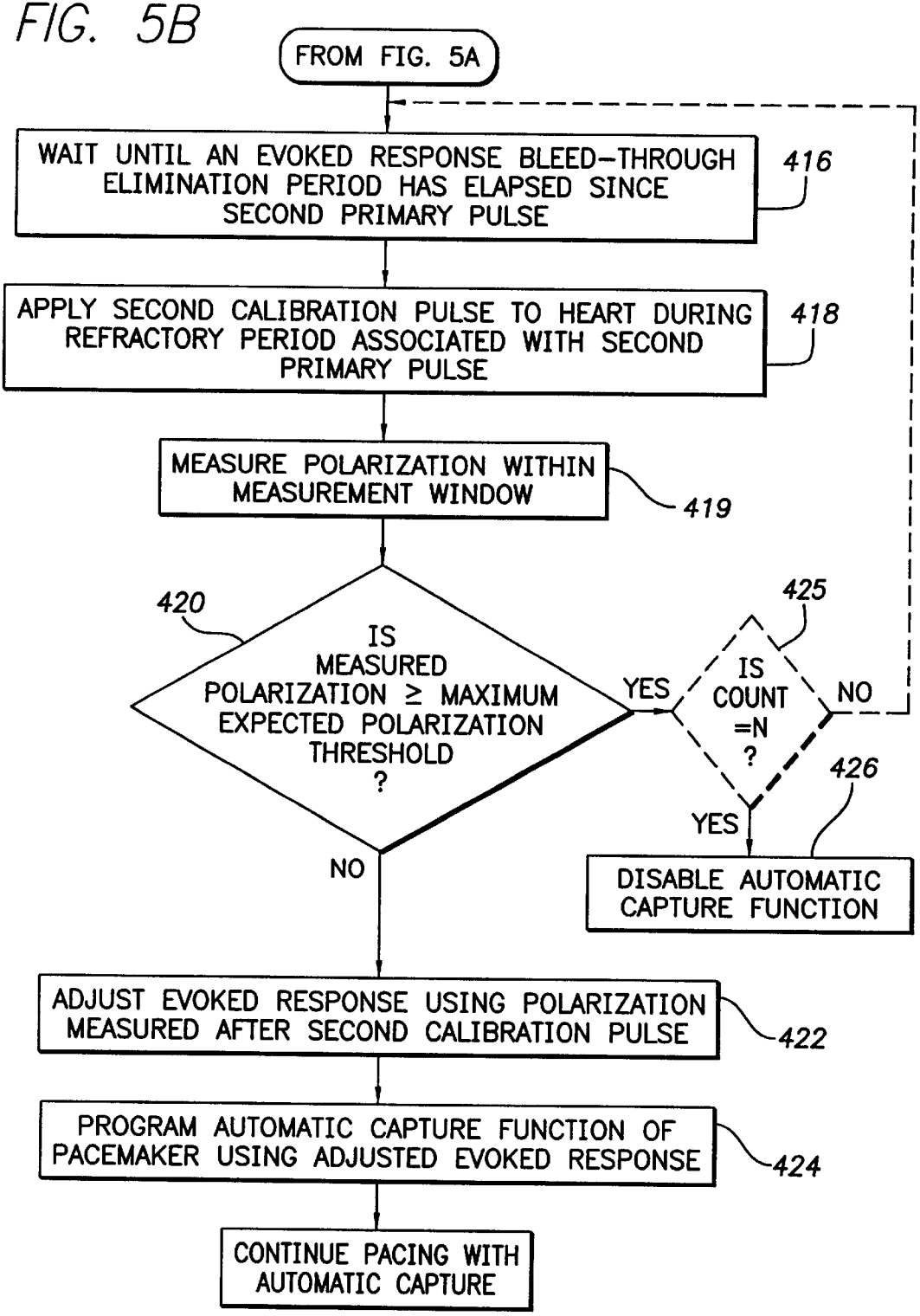

FIGS. 5A and 5B illustrate an alternative implementation where three consecutive pulses are applied, rather than two pairs of pulses. Many of the steps of the alternative implementation are the same as those of the method of FIGS. 3A and 3B and will only be described briefly. Referring first to FIG. 5A, at steps 400 and 402, a first primary pulse is applied and an evoked response is measured. At steps 404 and 406, a first calibration pulse is applied and a first polarization measurement is made. At step 408, the polarization is compared with a threshold and, if the polarization does not exceed the threshold, the measured evoked response is adjusted by the polarization value and the automatic capture function is programmed at steps 410 and 412. If the polarization exceeds the threshold, indicative of possible evoked response bleed-through, then processing proceeds to step 416 (see FIG. 5B) where the pacemaker waits until an evoked response bleed-through elimination period has elapsed. This period is measured from the primary pulse. Hence, the time between the primary pulse and the first calibration pulse is added to time elapsed since the first calibration pulse to determine the total bleed-through elimination period. In an exemplary embodiment, the bleed-through elimination period has a duration of about 200 milliseconds.

At step 418, a second calibration pulse is applied to the heart. Then, at step 419, a second polarization measurement is made and, at step 420, a determination is made as to whether the second polarization measurement also exceeds the threshold. If not, then the second polarization measurement is used to adjust the evoked response for the purposes of programming the automatic capture function at steps 422 and 424. If the polarization measurement exceeds the threshold, then the automatic capture function is disabled at step 426. Alternatively, as previously described in reference to step 231, additional "second" calibration pulses may be delivered via steps 425, 416 and 418 in order to search for an acceptably low polarization response.

The sequence of three pulses generated by the method of FIGS. 5A and 5B is illustrated in FIG. 6. Briefly, a primary pulse 500 evokes a response 502. Polarization is measured after a first calibration pulse 504. If the measured polarization amount exceeds a polarization threshold 506, then a second calibration pulse 508 is applied evoking a second amount of polarization. If the second amount of polarization is below the threshold 506, the second amount is used to adjust the evoked response detected following the primary pulse for the purposes of programming the automatic capture mechanism. Otherwise, automatic capture is disabled via step 426. In this manner, the effects of evoked response bleed-through are minimized or eliminated completely. Alternatively, additional "second" calibration pulses may be delivered (not shown) as described in reference to steps 425, 416, and 418.

In the embodiment of FIGS. 5A, 5B and 6, the measurement of the polarization associated with the first calibration pulse and the comparison of that polarization with the polarization threshold must be performed sufficiently promptly to permit a decision to be made as to whether to administer the second calibration pulse. Accordingly, a microprocessor or other circuit performing the calculations should have sufficient processing power to perform the calculations in a timely manner. In yet another embodiment, the second calibration pulse is automatically applied, regardless of the amount of polarization detected following the first calibration pulse. Thereafter, the pacemaker uses the second polarization amount for adjusting the evoked response only if the first amount was found to exceed the threshold. In this manner, the comparison of the first polarization amount with the threshold need not be performed prior to administering the second calibration pulse. In still other embodiments, the first and second polarization amounts may be combined or averaged. In still other embodiments, additional calibration pulses may be utilized.

Figure 7A:
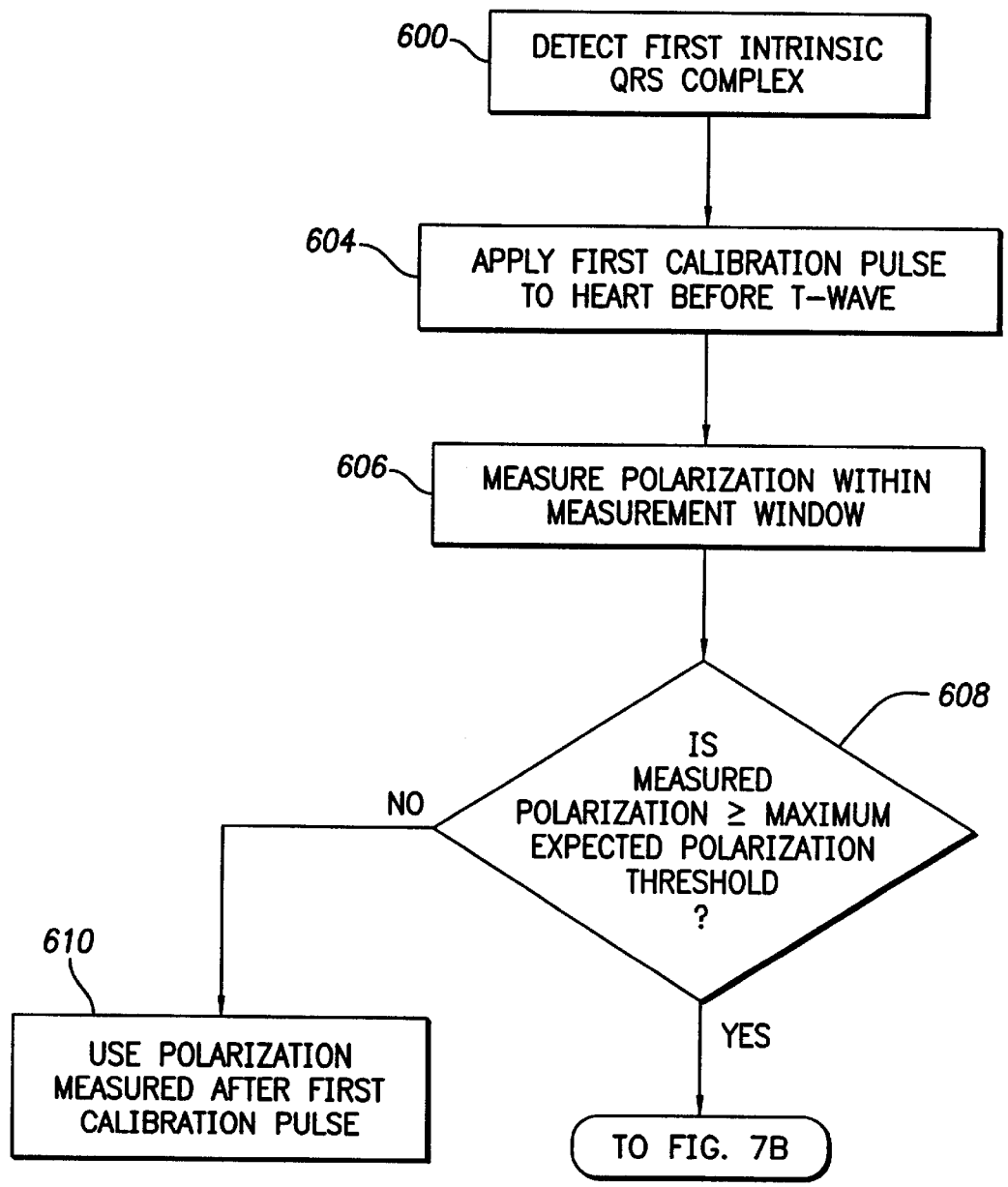
FIGS. 7A and 7B are flow charts illustrating another alternative method for measuring electrical polarization where polarization calibration pulses are administered following intrinsic QRS complexes.
Figure 7B:
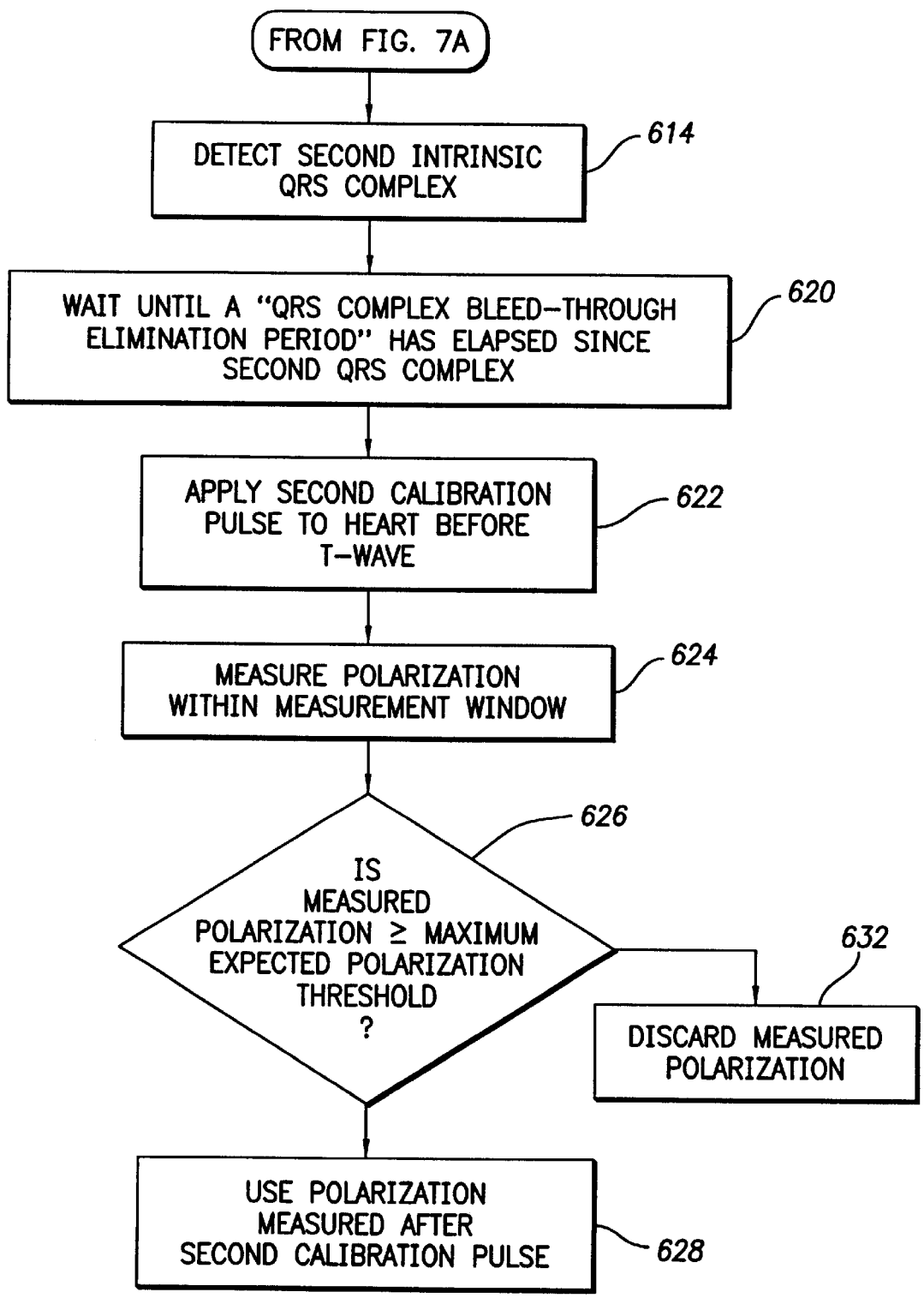

FIGS. 7A and 7B illustrate an alternative implementation where intrinsic depolarization events are exploited such that an initial evoked response need not be generated by application of a primary pulse. Rather, the evoked response arises naturally and calibration pulses are administered after the intrinsic evoked response. Many of the steps of this alternative implementation are the same as those described above with reference to the preceding implementations and therefore will only be described briefly. Referring first to FIG. 7A, at step 600, an intrinsic QRS complex is detected. At step 604, a first calibration pulse is applied before the subsequent T-wave and, at step 606, a first polarization measurement is made. At step 608, the polarization is compared with a predetermined threshold and, if the polarization does not exceed the threshold, the measured polarization is used in step 610 to adjust a previously detected evoked response. If the polarization exceeds the threshold, indicating that the QRS complex may not have completely decayed prior to the polarization measurement, then processing proceeds to steps 614 and 620 of FIG. 7B where the pacemaker waits until a QRS complex bleed-through elimination period has elapsed since a second QRS complex. This period is measured from the detection of the second QRS complex. At step 622, a second calibration pulse is applied before the subsequent T-wave and, at step 624, a second polarization measurement is made. The second measured polarization is then compared against the threshold at step 626 and, if it exceeds the threshold, the polarization value is discarded in step 632. If not, the polarization measurement is used at step 628, for example, to adjust a previously measured evoked response for the purposes of reprogramming an automatic capture function.

Figure 8:
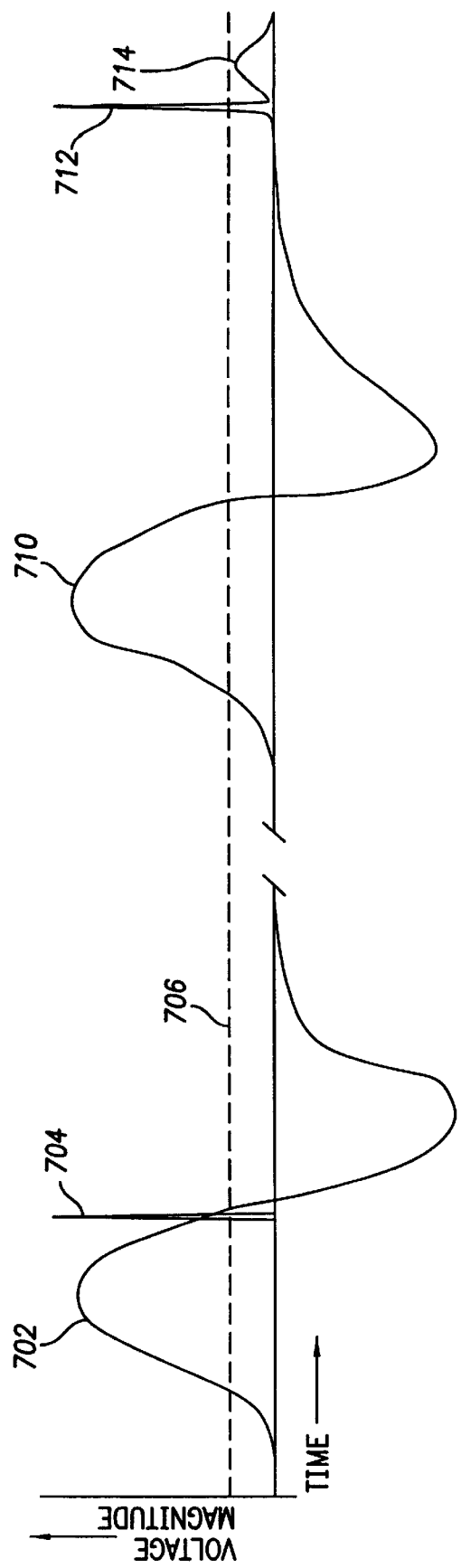
FIG. 8 is a timing diagram illustrating the use of the polarization calibration pulse of the method of FIGS. 5A and 5B.

The sequence of QRS complexes and calibration pulses employed by the method of FIGS. 7A and 7B is illustrated in FIG. 8. Briefly, a first QRS complex 702 is detected, then a first calibration pulse 704 is applied following detection of the QRS complex but before a next T-wave (not shown). The time delay between detection of the QRS complex and the generation of the first calibration pulse 704 is preferably set to a value to ensure that, in most cases, the QRS complex had decayed substantially. This value may be determined by appropriate experimentation. As can be seen, however, in the example of FIG. 8, the QRS complex has not fully decayed prior to the calibration pulse 704. Accordingly, the amount of polarization measured following the calibration pulse 704 may be affected by the QRS complex 710 and therefore may be erroneous. Thus, the pacemaker waits until a second intrinsic QRS complex 710 is detected and then generates a second calibration pulse 712 following a greater delay period provided to help ensure that the QRS complex 710 has fully decayed. Hence, the time delay between the second QRS complex 710 and the second calibration pulse 712 is greater than the time delay between the first QRS complex 702 and the first calibration pulse 704. The increase in the time delay period is set to a value sufficient (except in very rare cases) to ensure that the QRS complex has adequately decayed. Again, this value may be determined based upon appropriate experimentation. Note that the QRS complex has both positive and negative voltage portions. Depending upon when the polarization measurement is taken, the QRS complex may therefore either increase or decrease the magnitude of the detected polarization measurement. Accordingly, preferably, the absolute value of the polarization measurement is compared against a positive threshold.

Thus, a variety of techniques have been described in accordance with various aspects of the invention for making polarization measurements using an implantable cardiac stimulation device, such as a pacemaker. In the following, an overview of a stimulation device which may be configured to perform the above-described methods is provided. Depending upon the particular implementation of the invention, the configuration or programming of the stimulation device described below may need to be modified, as may be done by those skilled in the art.

Figure 9:
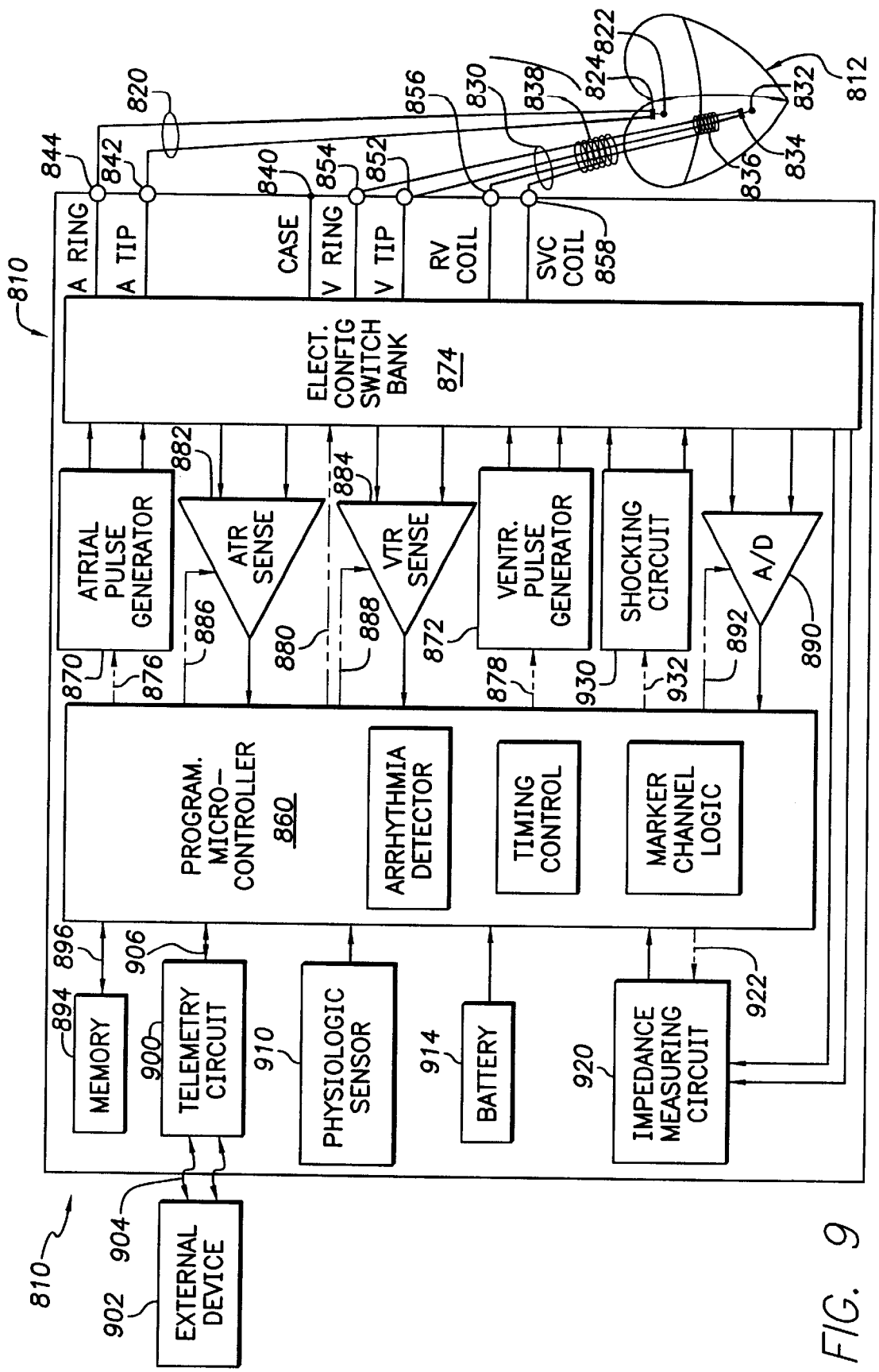
FIG. 9 is a functional block diagram of a dual-chamber implantable stimulation device illustrating the basic elements of a stimulation device which can be configured to perform the various methods of FIGS. 3A–8.

In FIG. 9, a simplified block diagram is shown of a dual-chamber implantable stimulation device 810 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation or adding circuitry to provide a device capable of treating three or four chambers.

To provide atrial chamber pacing stimulation and sensing, the stimulation device 810 is shown in electrical communication with a patient's heart 812 by way of an implantable right atrial lead 820 having an atrial tip electrode 822 and an atrial ring electrode 824 which typically is implanted in the patient's right atrial appendage. Stimulation device 810 may also be in electrical communication with the patient's heart by way of an implantable left atrial lead 821 (not shown) having and atrial tip electrode 823 and an atrial ring electrode 825 implanted in the patient's left atrial appendage. Accordingly, the implantable device is capable of independent stimulation and sensing in both the left and right atria.

The stimulation device 810 is also shown in electrical communication with the patient's heart 812 by way of an implantable right ventricular lead 830 having, in this embodiment, a right ventricular tip electrode 832, a ventricular ring electrode 834, a right ventricular (RV) coil electrode 836, and a superior vena cava (SVC) coil electrode 838. Typically, the right ventricular lead 830 is transvenously inserted into the heart 812 so as to place the RV coil electrode 836 in the right ventricular apex, and the SVC coil electrode 838 in the superior vena cava. Accordingly, the ventricular lead 830 is capable of receiving cardiac signals, and delivering stimulation in the form of pacing and shock therapy to the right ventricle. The stimulation device 810 may also be in communication with the heart 812 by way of a left ventricular lead 831 (not shown) having a tip electrode 833, a ring electrode 835, and a left ventricular (LV) coil electrode 837. Although not specifically shown, the left ventricular lead may also have an SVC coil electrode. Accordingly, the left ventricular lead 831 is capable of receiving cardiac signals, and delivering stimulation in the form of pacing and shock therapy, to the left ventricle.

While only four leads are described in reference to FIG. 9, it is to be understood that additional stimulation leads (with one or more pacing, sensing and/or shocking electrodes) may be used in order to efficiently and effectively provide pacing stimulation to the specific positions of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of such a coronary sinus lead, see U.S. patent application Ser. No. 09/457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The housing 840 (shown schematically) for the stimulation device 810 includes a connector (not shown) having an atrial tip terminal 842 and an atrial ring terminal 844, which are adapted for connection to the atrial tip electrode 822 and the atrial ring electrode 824, respectively. The housing 840 further includes a ventricular tip terminal 852, a ventricular ring terminal 854, a ventricular shocking terminal 856, and an SVC shocking terminal 858, which are adapted for connection to the ventricular tip electrode 832, the ventricular ring electrode 834, the RV coil electrode 836, and the SVC coil electrode 838, respectively. The housing 840 (often referred to as the "can", "case" or "case electrode") may be programmably selected to act as the return electrode, or anode, alone or in combination with one of the coil electrodes, 836 and 838. For convenience, the names of the electrodes are shown next to the terminals.

At the core of the stimulation device 810 is a programmable microcontroller 860 which controls the various modes of stimulation therapy. As is well known in the art, the microcontroller 860 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 860 includes the ability to process or monitor input signals (data) as controlled by a program code stored in a designated block of memory. The details of the design and operation of the microcontroller 860 are not critical to the present invention. Rather, any suitable microcontroller 860 may be used that carries out the functions described herein. The use of microprocessor-based control circuits for performing timing and data analysis functions is well known in the art. As shown in FIG. 9, an atrial pulse generator 870 and a ventricular pulse generator 872 generate pacing stimulation pulses for delivery by the atrial lead 820 and the ventricular lead 830, respectively, via a switch bank 874. The pulse generators, 870 and 872, are controlled by the microcontroller 860 via appropriate control signals, 876 and 878, respectively, to trigger or inhibit the stimulation pulses. The microcontroller 860 further includes timing circuitry that controls the operation of the stimulation device timing of such stimulation pulses, that is known in the art. The microcontroller 860 also includes an automatic capture threshold detection system employing the method described above.

The switch bank 874 includes a plurality of switches for switchably connecting the desired electrodes to the appropriate I/O circuits, thereby providing complete electrode programmability. Accordingly, the switch bank 874, in response to a control signal 880 from the microcontroller 860, determines the polarity of the stimulation pulses (e.g., unipolar or bipolar) by selectively closing the appropriate combination of switches (not shown) as is known in the art.

An atrial sense amplifier 882 and a ventricular sense amplifier 884 are also coupled to the atrial and ventricular leads 820 and 830, respectively, through the switch bank 874 for detecting the presence of cardiac activity. The switch bank 874 determines the "sensing polarity" of the cardiac signal by selectively closing the appropriate switches, as is also known in the art. In this way, the clinician may program the sensing polarity independent of the stimulation polarity.

Each sense amplifier, 882 and 884, preferably employs a low power, precision amplifier with programmable gain and/or automatic gain control, bandpass filtering, and a threshold detection circuit, known in the art, to selectively sense the cardiac signal of interest. The automatic gain control enables the device 810 to deal effectively with the difficult problem of sensing the low frequency, low amplitude signal characteristics of ventricular fibrillation. The outputs of the atrial and ventricular sense amplifiers, 882 and 884, are connected to the microcontroller 860 which, in turn, inhibit the atrial and ventricular pulse generators, 870 and 872, respectively, in a demand fashion whenever cardiac activity is sensed in the respective chambers.

For arrhythmia detection, the invention utilizes the atrial and ventricular sense amplifiers, 882 and 884, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 860 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 890. The data acquisition system 890 is configured to acquire intracardiac electrogram signals, convert the raw analog data into a digital signal, and store the digital signals for later processing and/or telemetric transmission to an external device 902. The data acquisition system 890 is coupled to the atrial and ventricular leads, 820 and 830, through the switch bank 874 to sample cardiac signals across any pair of desired electrodes.

The microcontroller 860 is further coupled to a memory 894 by a suitable data/address bus 896, where the programmable operating parameters used by the microcontroller 860 are stored and modified, as required, in order to customize the operation of the stimulation device 810 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 812 within each respective tier of therapy. Advantageously, the operating parameters of the implantable device 810 may be non-invasively programmed into the memory 894 through a telemetry circuit 900 in telemetric communication with an external device 902, such as a programmer, transtelephonic transceiver, or a diagnostic system analyzer. The telemetry circuit 900 is activated by the microcontroller 860 by a control signal 906. The telemetry circuit 900 advantageously allows intracardiac electrograms and status information relating to the operation of the device 810 (as contained in the microcontroller 860 or memory 894) to be sent to the external device 902 through an established communication link 904.

In the preferred embodiment, the stimulation device 810 further includes a physiologic sensor 910. Such sensors are commonly called "rate-responsive" sensors. The physiological sensor 910 is used to detect the exercise state of the patient, to which the microcontroller 860 responds by adjusting the rate and AV Delay at which the atrial and ventricular pulse generators, 870 and 872, generate stimulation pulses. The type of sensor used is not critical to the invention and is shown only for completeness. The stimulation device additionally includes a battery 914 which provides operating power to all of the circuits shown in FIG. 9. For the stimulation device 810, which employs shocking therapy, the battery must be capable of operating at low current drains for long periods of time (preferably less than 10 $\mu$a), and then be capable of providing high-current pulses (for capacitor charging) when the patient requires a shock pulse (preferably, in excess of 2 A, at voltages above 2 V, for periods of 10 seconds or more). The battery 914 must also have a predictable discharge characteristic so that elective replacement time can be detected. Accordingly, the invention preferably employs lithium/silver vanadium oxide batteries, as is currently true for most (if not all) such devices. As further shown in FIG. 9, the invention preferably includes an impedance measuring circuit 920 which is enabled by the microcontroller 860 by a control signal 922. The impedance measuring circuit 920 is not critical to the invention and is shown for only completeness.

Depending upon the implementation, the device may function as an implantable cardioverter/defibrillator (ICD) device. That is, it detects the occurrence of an arrhythmia, and automatically applies an appropriate electrical shock therapy to the heart aimed at terminating the detected arrhythmia. To this end, the microcontroller 860 further controls a shocking circuit 930 by way of a control signal 932. The shocking circuit 930 generates shocking pulses of low (up to 0.5 joules), moderate (0.5–10 joules), or high energy (11–40 joules), as controlled by the microcontroller 860. Such shocking pulses are applied to the patient's heart through at least two shocking electrodes, and as shown in this embodiment, using the RV and SVC coil electrodes, 836 and 838, respectively. In alternative embodiments, the housing 840 may act as an active electrode in combination with the RV electrode 836 alone, or as part of a split electrical vector using the SVC coil electrode 838 (i.e., using the RV electrode 836 as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 860 is capable of controlling the synchronous or asynchronous delivery of the shocking pulses.

As can be appreciated, a wide variety of techniques are consistent with the general principles of the invention. The embodiments described herein are merely illustrative of aspects of the invention and should not be construed as limiting the scope of the invention which is to be interpreted in accordance with the claims that follow.

What is claimed is:

1. A method for determining an amount of polarization occurring following generation of electrical pulses in heart tissue from an implantable cardiac stimulation device, the method comprising the steps of:

delivering a first pair of electrical pulses separated by a first amount of time to measure a magnitude of electrical polarization occurring within the heart tissue; and if the magnitude of electrical polarization exceeds a predetermined threshold, delivering a second pair of electrical pulses separated by a second amount of time, different than the first amount of time, to re-measure the magnitude of electrical polarization.

2. The method of claim 1 wherein the second amount of time is greater than the first amount of time.

3. The method of claim 2 wherein the first amount of time is between 60 and 90 milliseconds and wherein the second amount of time is between 40 and 200 milliseconds.

4. The method of claim 1 wherein the step of measuring the magnitude of electrical polarization occurring within the heart tissue using a first pair of electrical pulses comprises the steps of:

generating a first primary pulse sufficient to produce an evoked response within the heart tissue, wherein the first primary pulse causes the heart to become refractory for a first refractory period;

waiting the first amount of time, wherein the first amount of time is less than the first refractory period, and then generating a first calibration pulse; and detecting the magnitude of electrical polarization occurring within the heart tissue following the first calibration pulse but still during the first refractory period.

5. The method of claim 4 wherein the step of re-measuring the magnitude of electrical polarization occurring within the heart tissue using a second pair of electrical pulses comprises the steps of:

waiting for the first refractory period to elapse;

generating a second primary pulse sufficient to produce another evoked response within the heart tissue, wherein the second primary pulse causes the heart to become refractory for a second refractory period;

waiting the second amount of time, wherein the second amount of time is less than the second refractory period, and then generating a second calibration pulse; and detecting the magnitude of electrical polarization occurring within the heart tissue following the second calibration pulse but still during the second refractory period.

6. The method of claim 5 wherein the first and second primary pulses are substantially equal in magnitude to one another.

7. The method of claim 1 further including the steps of:

wherein the first: pair of electrical pulses and the second pair of electrical pulses each generates an evoked response;

measuring the magnitude of the evoked response generated by each pair of pulses.

8. The method of claim 7 further including the steps of:

if the magnitude of electrical polarization measured using the first pair of pulses does not exceed the predetermined threshold, adjusting the magnitude of the evoked response generated by the first pair of pulses by the magnitude of corresponding electrical polarization and programming an automatic capture function with the adjusted evoked response:, and if the magnitude of electrical polarization measured using the first pair of pulses exceeds the predetermined threshold, adjusting the magnitude of the evoked response generated by the second pair of pulses by the magnitude of corresponding electrical polarization and programming an automatic capture function with the adjusted evoked response.

9. The method of claim 8 further including the step of disabling the automatic capture function if the electrical polarization magnitudes measured using the first and second pair of pulses both exceed the predetermined threshold.

10. A system for determining an amount of polarization occurring following generation of electrical pulses in heart, the system comprising:

an implantable cardiac stimulation device to stimulate the heart tissue;

a first pair of electrical pulses separated by a first amount of time, the first pair of electrical pulses delivered by the implantable cardiac stimulation device;

means for measuring a magnitude of electrical polarization occurring within the heart tissue resulting from the first pair of electrical pulses;

means for determining whether the magnitude of electrical polarization exceeds a predetermined threshold;

if the magnitude of electrical polarization exceeds the predetermined threshold, a second pair of electrical pulses separated by a second amount of time, different than the first amount of time, the second pair of electrical pulses delivered by the implantable cardiac stimulation device; and means, responsive to a determination that the magnitude of electrical polarization exceeds a predetermined threshold, for re-measuring the magnitude electrical polarization delivered by the second pair of electrical.

11. The system of claim 10 wherein the second amount of time is greater than the first amount of time.

12. The system of claim 11 wherein the first amount of time is between 60 and 90 milliseconds and wherein the second amount of time is between 40 and 200 milliseconds.

13. The system of claim 10 wherein the means for measuring the magnitude of electrical polarization occurring within the heart tissue using a first pair of electrical pulses comprises:

means for generating a first primary pulse sufficient to produce an evoked response within the heart tissue, wherein the first primary pulse causes the heart to become refractory for a first refractory period;

means for waiting the first amount of time, wherein the first amount of time is less than the first refractory period, and then for generating a first calibration pulse; and means for detecting the magnitude of electrical polarization occurring within the heart tissue following the first calibration pulse but still during the first refractory period.

14. The system of claim 13 wherein the means for re-measuring the magnitude of electrical polarization occurring within the heart tissue using a second pair of electrical pulses comprises:

means for waiting for the first refractory period to elapse;

means for generating a second primary pulse sufficient to produce another evoked response within the heart tissue, wherein the second primary pulse causes the heart to become refractory for a second refractory period;

means for waiting the second amount of time, wherein the second amount of time is less than the second refractory period, and then for generating a second calibration pulse; and means for detecting the magnitude of electrical polarization occurring within the heart tissue following the second calibration pulse but still during the second refractory period.

15. The system of claim 14 wherein the first and second primary pulses are substantially equal in magnitude to one another.

16. The system of claim 10 further including means for measuring the magnitude of the evoked response generated by each pair of pulses.

17. The system of claim 16 further including:

means, responsive to a determination that the magnitude of electrical polarization measured using the first pair of pulses does not exceed the predetermined threshold, for adjusting the magnitude of evoked response generated by the first pair of pulses by the magnitude of corresponding electrical polarization and programming an automatic capture function with the adjusted evoked response; and means, responsive to a determination that the magnitude of electrical polarization measured using the first pair of pulses exceeds the predetermined threshold, for adjusting the magnitude of evoked response generated by the second pair of pulses by the magnitude of corresponding electrical polarization and programming an automatic capture function with the adjusted evoked response.

18. The system of claim 17 further including means, responsive to a determination that the magnitudes of electrical polarization measured using the first pair and the second pair of pulses both exceed the predetermined threshold, for disabling the automatic capture function.

19. A system for determining an amount of polarization occurring following generation of electrical pulses in heart tissue, the system comprising:

an implantable cardiac stimulation device to stimulate the heart tissue;

a first pair of electrical pulses separated by a first amount of time, the first pair of electrical pulses delivered by the implantable cardiac stimulation device;

an electrical polarization measurement unit for measuring a magnitude of electrical polarization occurring within the heart tissue by delivering the first pair of electrical pulses;

a threshold comparison unit for determining whether the magnitude of electrical polarization exceeds a predetermined threshold, if the magnitude of electrical polarization exceeds the predetermined threshold, a second pair of electrical pulses separated by a second amount time, different than the first amount of time, the second pair of electrical pulses delivered by the implantable cardiac stimulation device;

a control unit, responsive to a determination that the magnitude of electrical polarization exceeds a predetermined threshold, for controlling the electrical polarization unit to re-measure the magnitude electrical polarization resulting from the second pair of electrical pulses.

20. A method comprising:

delivering a first pair of electrical pulses to heart tissue, the first pair of electrical pulses separated by a first amount of time;

measuring a magnitude of electrical polarization resulting from the first pair of electrical pulses;

if the magnitude of electrical polarization exceeds a predetermined threshold, delivering a second pair of electrical pulses to the heart tissue, the second pair of electrical pulses separated by a second amount of time, the second amount of time being different from the first amount of time;

re-measuring the magnitude of electrical polarization resulting from the second pair of electrical pulses; and if the magnitude of electrical polarization resulting from the second pair of electrical pulses is within the predetermined threshold, adjusting an evoked response in accordance with the magnitude of electrical polarization resulting from the second pair of electrical pulses.

21. The method of claim 20 further comprising:

if the magnitude of electrical polarization resulting from the second pair of electrical pulses exceeds the predetermined threshold, disabling an automatic capture function.

22. The method of claim 20 wherein the second amount of time is greater than the first amount of time.

23. The method of claim 20 wherein the first amount of time is between 60 and 90 milliseconds and wherein the second amount of time is between 40 and 200 milliseconds.

24. The method of claim 20 wherein the measuring the magnitude of electrical polarization resulting from the first pair of electrical pulses further comprises:

generating a first primary pulse sufficient to produce an evoked response within the heart tissue, wherein the first primary pulse causes the heart tissue to become refractory for a first refractory period;

waiting the first amount of time, wherein the first amount of time is less than the first refractory period, and then generating a first calibration pulse; and detecting the magnitude of electrical polarization occurring within the heart tissue following the first calibration pulse but still during the first refractory period.

25. The method of claim 24 wherein the re-measuring the magnitude of electrical polarization resulting from the second pair of electrical pulses further comprises:

waiting for the first refractory period to elapse;

generating a second primary pulse sufficient to produce another evoked response within the heart tissue, wherein the second primary pulse causes the heart tissue to become refractory for a second refractory period;

waiting the second amount of time, wherein the second amount of time is less than the second refractory period, and then generating a second calibration pulse; and detecting the magnitude of electrical polarization occurring within the heart tissue following the second calibration pulse but still during the second refractory period.

26. The method of claim 25 wherein the first and second primary pulses are substantially equal in magnitude to one another.

* * * * *